(12) United States Patent
Seth et al.

(10) Patent No.: US 10,124,140 B2
(45) Date of Patent: Nov. 13, 2018

(54) ATMOSPHERE CONDITIONING DEVICE

(71) Applicants: Ashoke Seth, Phoenix, AZ (US);
Rashmi Seth, Phoenix, AZ (US)

(72) Inventors: Ashoke Seth, Phoenix, AZ (US);
Rashmi Seth, Phoenix, AZ (US)

(\*) Notice: Subject to any disclaimer, the term of this patent is extended or adjusted under 35 U.S.C. 154(b) by 99 days.

(21) Appl. No.: 15/241,174

(22) Filed: Aug. 19, 2016

(65) Prior Publication Data

US 2017/0072355 A1 Mar. 16, 2017

Related U.S. Application Data

(60) Provisional application No. 62/217,867, filed on Sep. 12, 2015.

(51) Int. Cl.
| | |
|---|---|
| *A61M 16/10* | (2006.01) |
| *A61L 9/00* | (2006.01) |
| *F24F 3/16* | (2006.01) |
| *A61M 16/00* | (2006.01) |
| *F24F 1/00* | (2011.01) |
| *A61L 9/12* | (2006.01) |

(52) U.S. Cl.
CPC ............ *A61M 16/105* (2013.01); *A61L 9/00* (2013.01); *F24F 3/1603* (2013.01); *A61L 9/12* (2013.01); *A61M 16/0066* (2013.01); *A61M 2205/7545* (2013.01); *A61M 2205/8206* (2013.01); *A61M 2209/08* (2013.01); *F24F 2001/0096* (2013.01)

(58) Field of Classification Search
CPC .. B03C 3/32; B03C 3/00; B01D 19/00; B01D 46/00; B01D 50/00; B01D 46/46
USPC ...... 55/385.1, 413, 415, 416, 467, 471, 473, 55/482, 484, 498, 521, 524, 527, DIG. 34; 96/55, 66, 68, 154, 222, 397, 399, 417, 96/423; 454/358
See application file for complete search history.

(56) References Cited

U.S. PATENT DOCUMENTS

| | | | | |
|---|---|---|---|---|
| 4,902,315 | A * | 2/1990 | Spicer .................... | B01D 46/42 454/238 |
| 5,601,636 | A * | 2/1997 | Glucksman ........... | F24F 3/1603 55/356 |
| 5,762,665 | A * | 6/1998 | Abrahamian ........ | B01D 46/008 55/385.1 |
| 6,119,689 | A | 9/2000 | Korman | |
| 6,444,004 | B1 * | 9/2002 | Tang .................... | F04D 17/165 415/208.3 |

(Continued)

*Primary Examiner* — Duane Smith
*Assistant Examiner* — Minh Chau T Pham
(74) *Attorney, Agent, or Firm* — Patentfile, LLC; Bradley C. Fach; Steven R. Kick

(57) ABSTRACT

In some embodiments, an atmosphere conditioning device may include a housing which may form a cavity. An air inlet may be formed into the housing, and the air inlet may be in fluid communication with the cavity. A filter medium which may govern the entrance of atmosphere into the cavity may be coupled with the housing so that the filter medium may be in fluid communication with the cavity and the first air inlet. A first air outlet may be disposed on the first side of the housing, and the first air outlet may be in fluid communication with a first air motivator. The first air motivator may also be in fluid communication with the cavity and may motivate conditioned air, which has passed through the filter medium, from the cavity and out of the device through the first air outlet.

20 Claims, 8 Drawing Sheets

(56) References Cited

U.S. PATENT DOCUMENTS

| | | | |
|---|---|---|---|
| 7,025,798 B2 * | 4/2006 | Endo | B01D 46/0023 |
| | | | 55/385.1 |
| 7,118,608 B2 | 10/2006 | Lovell | |
| 7,543,585 B2 | 6/2009 | Torgerson | |
| 7,998,231 B2 * | 8/2011 | Zheng | A61L 9/16 |
| | | | 55/337 |
| 9,144,697 B2 | 9/2015 | Augustine et al. | |
| 9,205,218 B1 | 12/2015 | Bachan et al. | |
| 9,283,573 B2 * | 3/2016 | Nock | F04D 29/403 |
| 2011/0126828 A1 | 6/2011 | Wu et al. | |
| 2011/0236229 A1 * | 9/2011 | Fitton | F04D 29/703 |
| | | | 417/234 |
| 2012/0137876 A1 * | 6/2012 | Miller | B01D 46/0043 |
| | | | 95/23 |
| 2017/0097168 A1 * | 4/2017 | Chang | F24F 5/0042 |

* cited by examiner

ATMOSPHERE CONDITIONING DEVICE

CROSS REFERENCE TO RELATED APPLICATIONS

This application claims priority to and the benefit of the filing date of U.S. Provisional Application No. 62/217,867, filed on Sep. 12, 2015, entitled "BREATHING ASSISTANCE DEVICE", which is hereby incorporated by reference in its entirety.

FIELD OF THE INVENTION

This patent specification relates to the field of atmosphere conditioning devices. More specifically, this patent specification relates to an atmosphere conditioning device for improving the condition of the atmosphere proximate to the device.

BACKGROUND

Humans require an atmosphere of fresh air on a continuous basis. There are medical devices available to serve this purpose but they are cumbersome to carry around and use and are often very expensive. Even facial masks that people use to filter the air they are breathing are hot, cumbersome, and inconvenient to wear. The need for an atmosphere of fresh air is especially felt by people who have conditions like asthma or simply want to breathe cleaner air than the surroundings and currently do not have an inexpensive and convenient way to do so. It is an unfortunate and all too common experience that people have to breathe air from their surroundings that poses a threat to their health. Some examples of people in undesirable breathing situations include: passengers aboard a plane having to breathe air inside the passenger cabin and ending up with illness, discomfort, or other conditions that bother them; people who travel internationally and visit places with poor air quality; and people who go to places where smoking is allowed by law, such as a casino, but who do not smoke and end up inhaling second hand smoke which is very harmful.

Therefore, a need exists for novel atmosphere conditioning devices for improving the air which may be breathed by a user. There is a further need for novel atmosphere conditioning devices that will provide an opportunity to the user to breathe in significantly cleaner air very inexpensively. Finally, there exists a need for novel atmosphere conditioning devices which are not cumbersome or required to be worn by a user.

BRIEF SUMMARY OF THE INVENTION

An atmosphere conditioning device for improving the air which may be breathed by a user is provided. In some embodiments, the device may include a housing having a first side, a second side, and a perimeter which may form a cavity. An air inlet may be formed into the housing, and the air inlet may be in fluid communication with the cavity. A filter medium which may govern the entrance of atmosphere into the cavity may be coupled with the housing so that the filter medium may be in fluid communication with the cavity and the first air inlet. A first air outlet may be disposed on the first side of the housing, and the first air outlet may be in fluid communication with a first air motivator. The first air motivator may also be in fluid communication with the cavity and may motivate conditioned air, which has passed through the filter medium, from the cavity and out of the device through the first air outlet. As conditioned air exits the device, atmosphere is drawn into the air inlet, through the filter medium, and into the cavity as conditioned air to replace the conditioned air exiting the device through the first air outlet.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
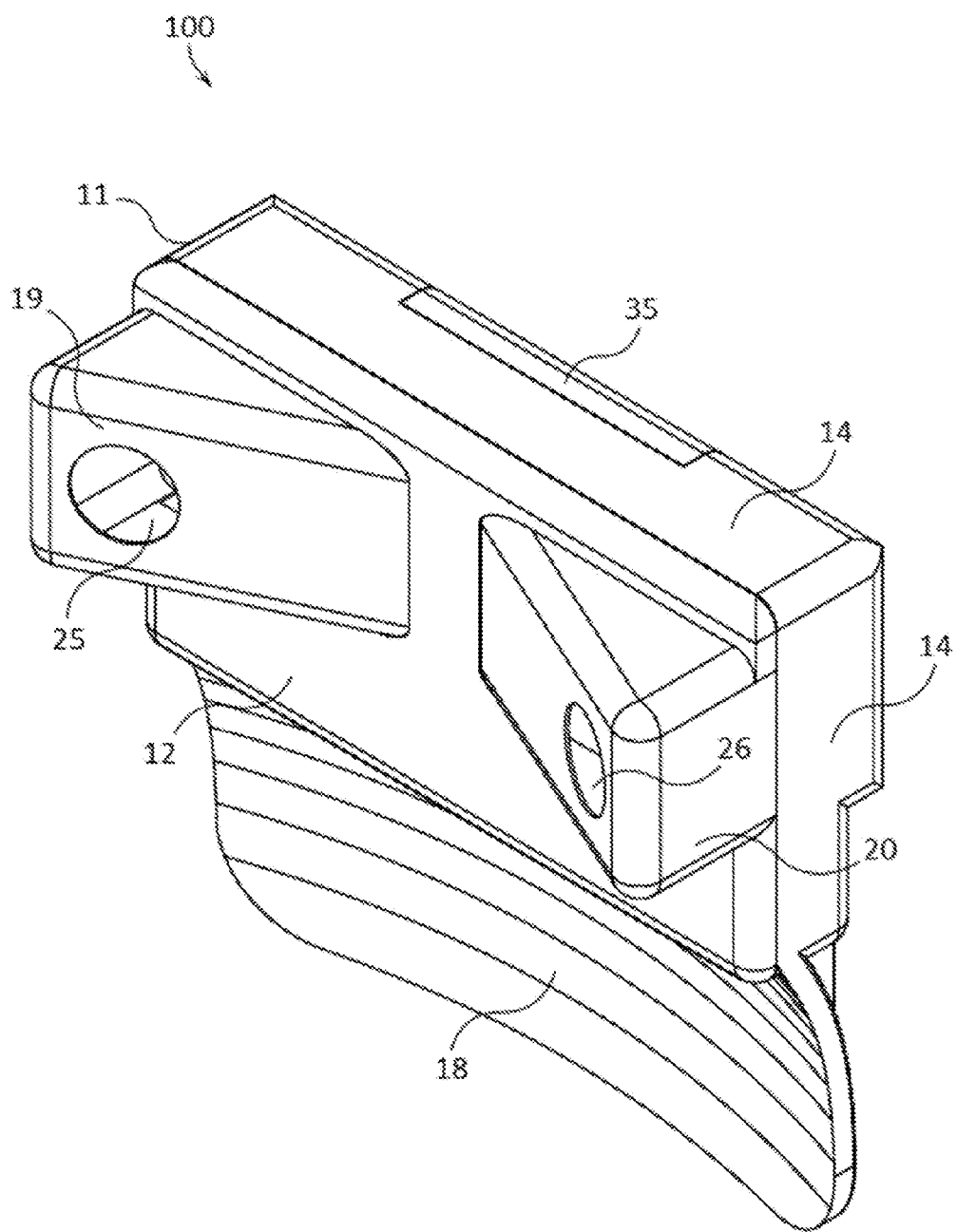
FIG. 1 depicts a front perspective view of an example of an atmosphere conditioning device according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

New atmosphere conditioning devices for improving the air which may be breathed by a user are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. An example of atmosphere conditioning device ("the device") 100 according to various embodiments is perhaps best illustrated in FIGS. 1, 2, 7, and 8. In some embodiments, the device 100 may comprise a housing 11 having a first side 12, a second side 13, and a perimeter 14 which may form a cavity 15. An air inlet 21 may be formed into the housing 11, and the air inlet 21 may be in fluid communication with the cavity 15. A filter medium 31 which may govern the entrance of atmosphere 201 into the cavity 15 may be coupled with the housing 11 so that the filter medium 31 may be in fluid communication with the cavity 15 and the first air inlet 21. A first air outlet 25 may be disposed on the first side 12 of the housing 11, and the first air outlet 25 may be in fluid communication with a first air motivator 41. The first air motivator 41 may also be in fluid communication with the cavity 15 and may motivate conditioned air 202, which has passed through the filter medium 31, from the cavity 15 and out of the device 100 through the first air outlet 25. As conditioned air 202 exits the device 100, atmosphere 201 is drawn into the air inlet 21, through the filter medium 31, and into the cavity 15 as conditioned air 202 to replace the conditioned air 202 exiting the device 100 through the first air outlet 25.

In preferred embodiments, the device 100 may further comprise a second air outlet 26 which may be disposed on the first side 12 of the housing 11 opposingly positioned to the first air outlet 25. The second air outlet 26 may be in fluid communication with a second air motivator 42. The second air motivator 42 may also be in fluid communication with the cavity 15 and may also motivate conditioned air 202, which has passed through the filter medium 31, from the cavity 15 and out of the device 100 through the second air outlet 26. As conditioned air 202 exits the device 100, atmosphere 201 is drawn into the air inlet 21, through the filter medium 31, and into the cavity 15 as conditioned air 202 to replace the conditioned air 202 exiting the device 100 through the second air outlet 26.

In alternative embodiments, the device 100 may comprise three or more air outlets, such as a first air outlet 25, second air outlet 26, third air outlet, fourth air outlet, fifth air outlet, sixth air outlet, seventh air outlet, or any number of air outlets. Furthermore, any number of air outlets 25, 26, may be disposed or positioned anywhere on the housing 11, such as on the first side 12, on the second side 13, and/or on the perimeter 14.

The housing 11 may be made from durable materials such as aluminum, steel, other metal and metal alloys, hard plastics, such as polyvinyl chloride (PVC), hard natural and synthetic rubber, wood, or any other generally rigid material. The first side 12, second side 13, and perimeter 14 may be configured in a plurality of sizes and shapes to form a housing 11 in a plurality of sizes and shapes. Optionally, the first side 12, second side 13, and/or perimeter 14 may comprise one or more protrusions, such as a first protrusion 19 and a second protrusion 20 or any other number of protrusions, depressions, or other structural features. In some embodiments, a first air outlet 25 may be disposed on or proximate to a first protrusion 19 and a second air outlet 26 may be disposed on or proximate to a second protrusion 20 so that the air outlets 25, 26, may be positioned away from the first side 12 in a desired manner thereby allowing conditioned air 202 exiting the air outlets 25, 26, to be directed in a desired manner. It should be understood to one of ordinary skill in the art that the first side 12, second side 13, perimeter 14, and therefore the housing 11 may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Figure 2:
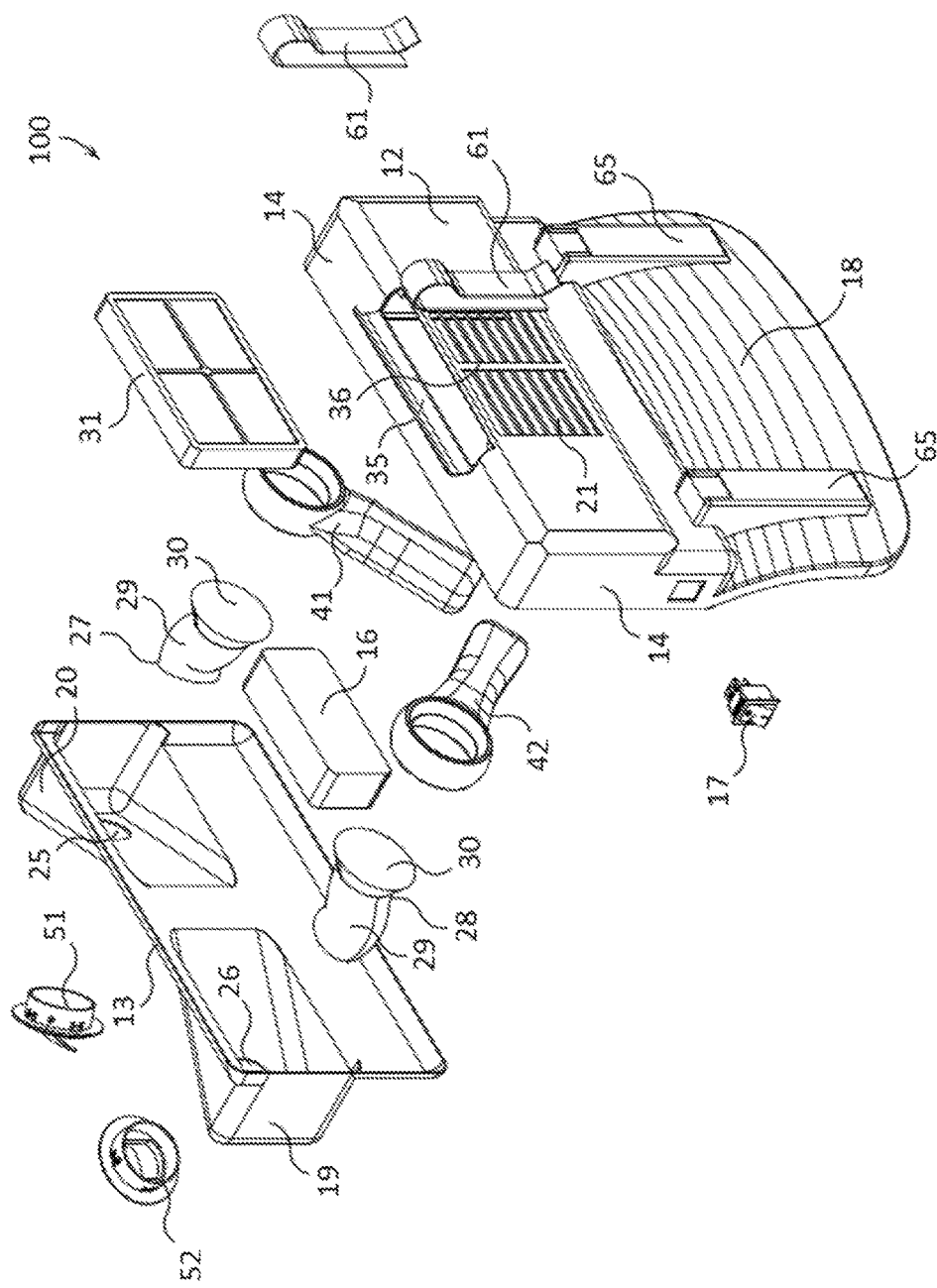
FIG. 2 illustrates a rear perspective exploded view of an example of an atmosphere conditioning device according to various embodiments described herein.

Turning to FIG. 2, in some embodiments, the device 100 may comprise a power source 16 which may provide electrical power to any component of the device 100 that may require electrical power such as to one or more air motivators 41, 42. A power source 16 may comprise a battery, such as a lithium ion battery, nickel cadmium battery, alkaline battery, or any other suitable type of battery, a fuel cell, a capacitor, a super capacitor, or any other type of energy storing and/or electricity releasing device. In further embodiments, a power source 16 may comprise a power cord, kinetic or piezo electric battery charging device, a solar cell or photovoltaic cell, and/or inductive charging or wireless power receiver.

Additionally, the device 100 may comprise one or more user control inputs 17 that a user may interact with such as turnable control knobs, depressible button type switches, a key pad, slide type switches, rocker type switches, or any other suitable input that may be used to modulate electricity to one or more air motivators 41, 42. The user control inputs 17 may be configured to control one or more functions of the device 100 such as to turn on or to turn off the air motivators 41, 42, and/or to modulate the speed of the air motivators 41, 42.

As perhaps best depicted in FIG. 2, in some embodiments, the device 100 may comprise one or more conduction conduits, such as a first conduction conduit 27 and a second conduction conduit 28. A conduction conduit 27, 28, may comprise a length of material of any size or shape forming a wall 29 which bounds a channel 30. The channel 30 may direct the movement of air to provide fluid communication between two elements such as between an air motivator 41, 42, and an air outlet 25, 26. In further embodiments, a first conduction conduit 27 may provide fluid communication between a first air motivator 41 and a first air outlet 25. Optionally, a second conduction conduit 28 may provide fluid communication between a second air motivator 42 and a second air outlet 26. In alternative embodiments, a single conduction conduit 27, 28, may provide fluid communication between a single air motivator 41, 42, and one or more air outlets 25, 26.

Figure 3:
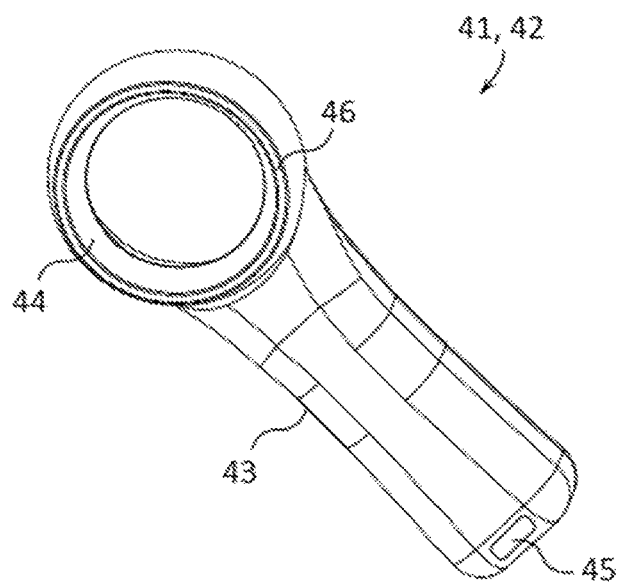
FIG. 3 shows a perspective view of an example of an air motivator according to various embodiments described herein.
Figure 9:
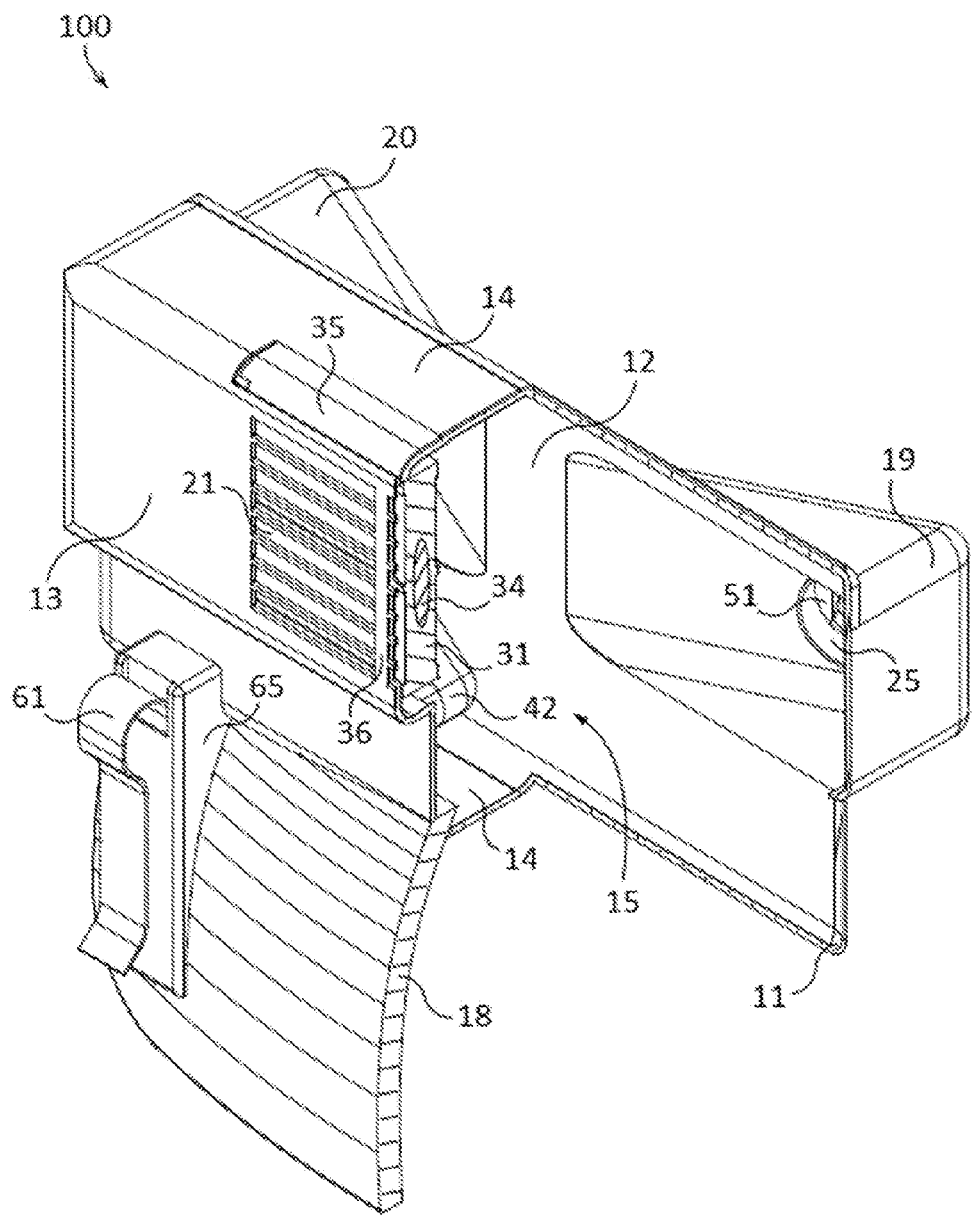
FIG. 9 shows a sectional, through line 9-9 shown in FIG. 8, rear perspective view of an example of an atmosphere conditioning device according to various embodiments described herein.
Figure 10:
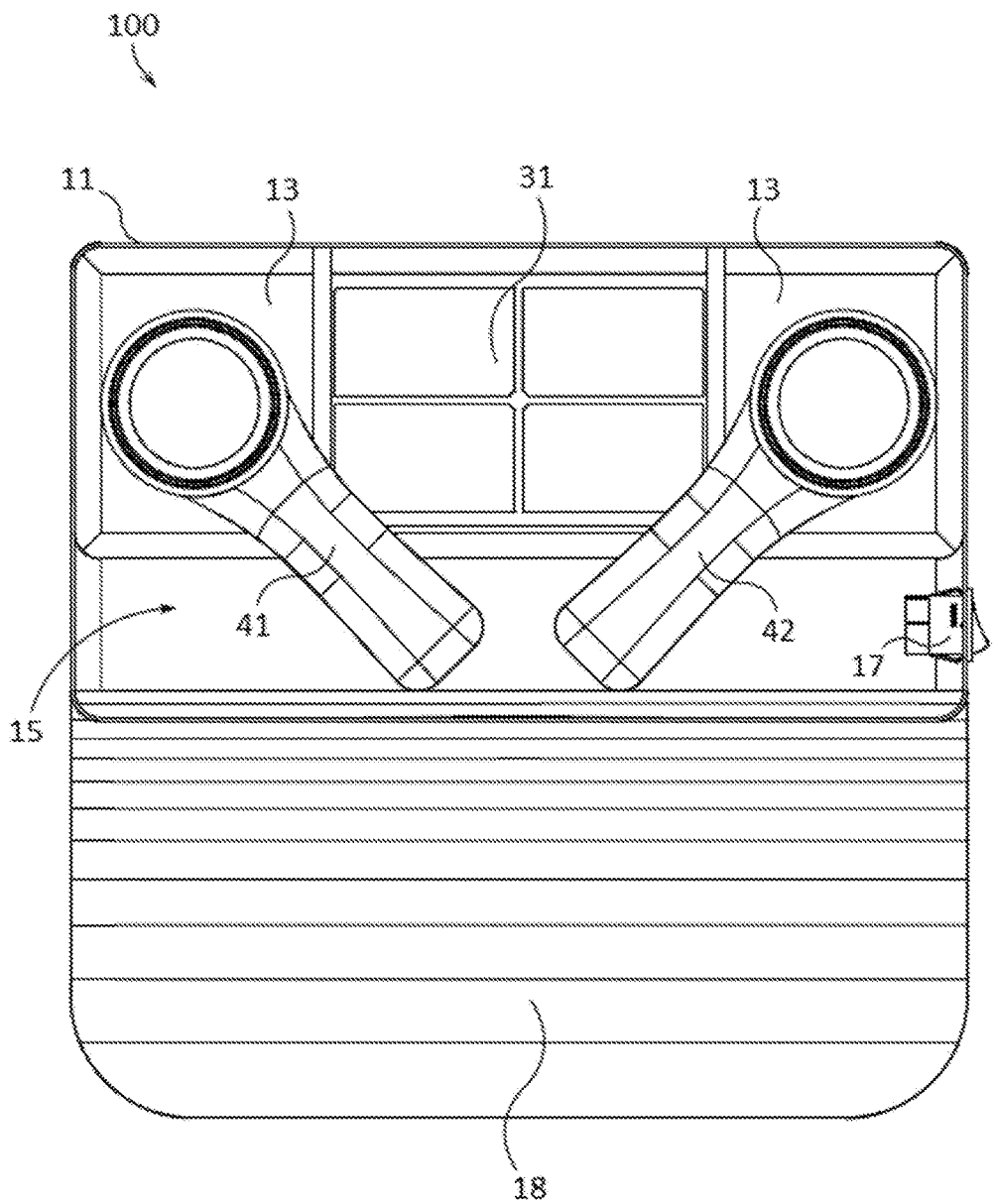
FIG. 10 depicts a front elevation view of an example of an atmosphere conditioning device with the first side removed according to various embodiments described herein.

FIG. 3 shows a perspective view of an example of an air motivator 41, 42, according to various embodiments described herein. In some embodiments, the device 100 may comprise one or more air motivators, such as a first air motivator 41, a second air motivator 42, a third air motivator, a fourth air motivator, or the like, which may function to move or motivate air and atmosphere from one location to another. In preferred embodiments, a device 100 comprising more than one air motivator, may comprise two or more air motivators of the same type. In this manner a first air motivator 41 and a second air motivator 42 may be substantially the same and differ many by positioning and which air outlet 25, 26, they motivate air through. In some embodiments, and as shown in FIGS. 9 and 10, one or more air motivators 41, 42, may be housed or disposed within the cavity, while in other embodiments, the one or more air motivators 41, 42, may be integrally formed with the housing 11 so that generally only the air or atmosphere motivation elements, of the air motivators 41, 42, may be in fluid communication with the cavity 15.

In some embodiments, an air motivator 41, 42, may be or comprise a fan generally described as a machine used to create flow within a fluid, typically a gas such as air. Typically, fans may include air or atmosphere motivation elements such as a rotating arrangement of vanes or blades which act on the fluid. The rotating assembly of blades and hub is commonly known as an impeller, a rotor, or a runner. Usually, it is contained within some form of housing or case 43. Optionally, a fan of an air motivator 41, 42, may be powered by one or more electric motors, but other types of motors and sources of power may be used. In preferred embodiments, an air motivator 41, 42, may be a bladeless fan (sometimes called an air multiplier) which blows air from a ring 44 with no external blades. Its blades are hidden in the case 43. The air is drawn in through an air intake 45 by a fan in the case 43 and then directed up into the ring 44 to exit through an aperture or crack 46 all around the ring 44 and passes over a shape like that of an aircraft wing. In alternative embodiments, an air motivator 41, 42, may be an axial-flow fan, a centrifugal fan, a cross-flow fan, or any other suitable device which is able to motivate a gas or air fluid.

Figure 4:
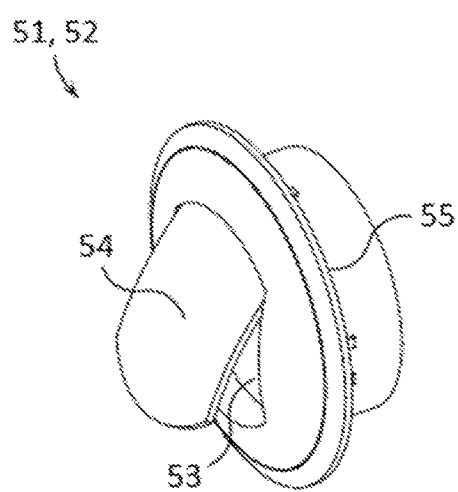
FIG. 4 depicts a perspective view of an example of an outlet governor according to various embodiments described herein.
Figure 8:
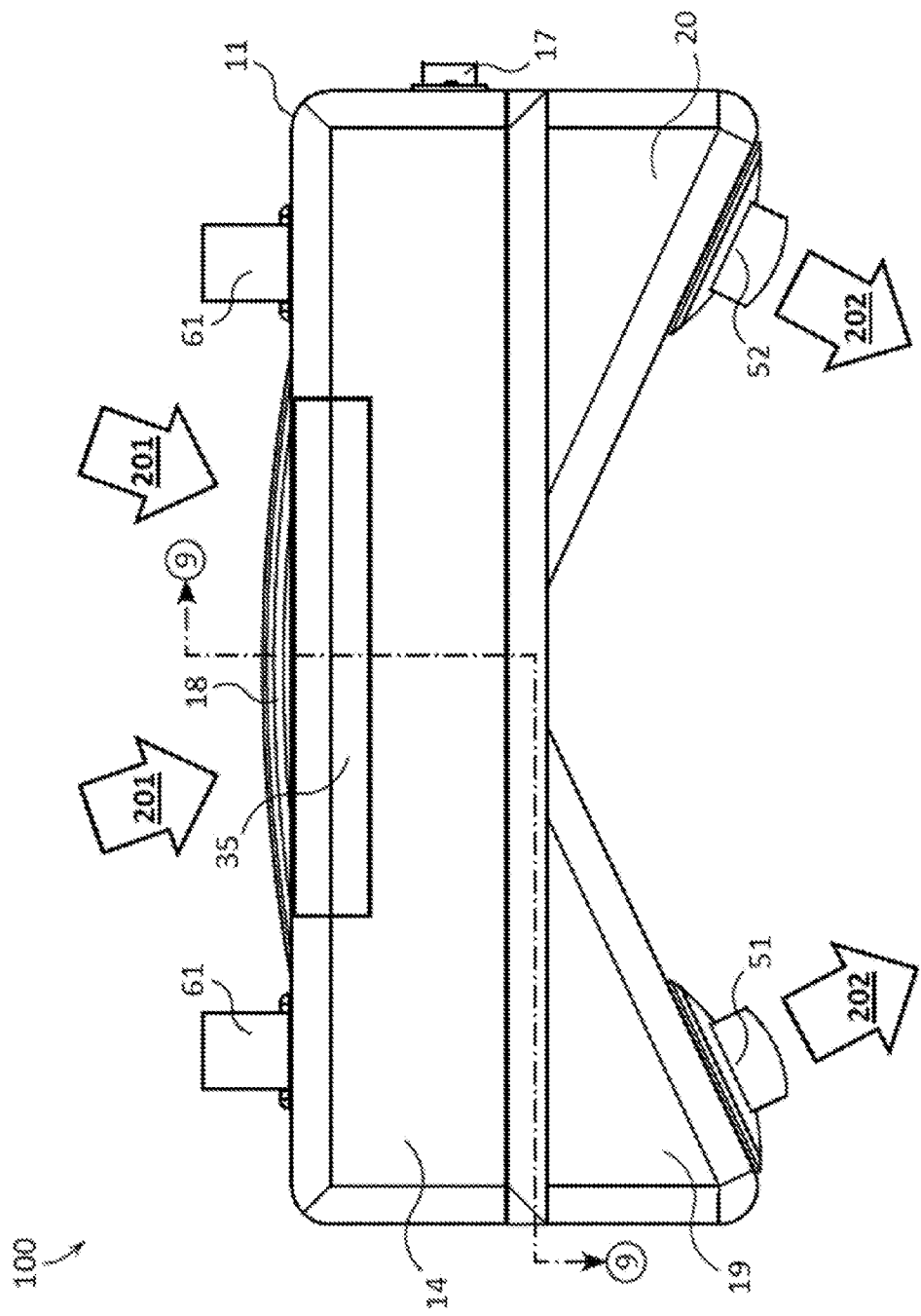
FIG. 8 illustrates a top plan view of an example of an atmosphere conditioning device according to various embodiments described herein.

FIG. 4 depicts a perspective view of an example of an outlet governor 51, 52, according to various embodiments described herein. In some embodiments and as shown in FIGS. 2, 8, and 9, the device 100 may comprise one or more outlet governors, such as a first outlet governor 51, second outlet governor 52, third outlet governor, fourth outlet governor, and the like. Generally, an outlet governor 51, 52, may function to direct and/or diffuse air, such as conditioned air 202, that is exiting the device 100 through an air outlet 25, 26. In preferred embodiments, a first outlet governor 51 may be coupled to a first air outlet 25 and a second outlet governor 52 may be coupled to a second air outlet 26. In further embodiments, an outlet governor 51, 52, may be rotationally coupled to the housing 11, an air outlet 25, 26, and/or a conduction conduit 27, 28, so that by rotating the outlet governor 51, 52, the direction of conditioned air 202 air exiting the device 100 may be changed. In still further embodiments, an outlet governor 51, 52, may comprise a directional aperture 53 which may be governed by a flap 54. Optionally, a flap 54 may be coupled to the body 55 of the outlet governor 51, 52, so that the directional aperture 53 may be opened or enlarged by pivoting a portion of the flap 54 away from the body 55 and closed or made smaller by pivoting a portion of the flap 54 towards from the body 55. In alternative embodiments, one or more flaps 54 may be coupled to the body 55 of the outlet governor 51, 52, so that by sliding, rotating, extending, retracting, or otherwise manipulation of the flaps 54 may result in opening, enlarging, closing, reducing, and/or changing the direction of a directional aperture 53.

Figure 5:
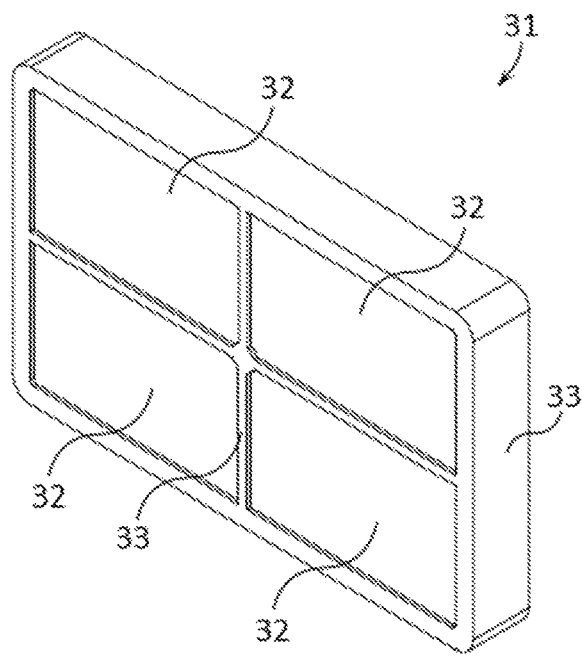
FIG. 5 illustrates a perspective view of an example of a filter medium according to various embodiments described herein.

FIG. 5 illustrates a perspective view of an example of a filter medium according to various embodiments described herein. In some embodiments, the device 100 may comprise one or more filter mediums 31 as shown in FIGS. 2, 7, 9, and 10. A filter medium 31 may be coupled with the housing 11 so that it is in fluid communication with the cavity 15 and with one or more air inlets 21. A filter medium 31 may comprise a filter material 32 and an optional frame 33 which may provide structural support to the filter material 32 and which may be made from a generally rigid material such as a rigid plastic or metal. The filter material 32 may be made from or comprise a matrix of synthetic fibers, such as polyester fibers, a matrix of natural fibers, such as cotton fibers and paper fibers, and/or any other filtration medium suitable for removing particulate matter from air or an atmosphere.

Optionally, the filter medium 31 may comprise an air enhancing material 34 which may be imparted or added to air which passes through the filter material 32. In some embodiments, the filter material 32 may be impregnated or otherwise permeated with an air enhancing material 34 which may sublimate, evaporate, or otherwise be imparted or added to air which passes through the filter material 32. In other embodiments, the filter medium 31 may comprise an air enhancing material 34 in the form of one or more scent releasing solid which may be coupled to or within the filter material 32 and or frame 33. Examples of air enhancing materials 34 may include a fragrance releasing liquid, such as Febreeze®, and a fragrance releasing crystal, such as Crystal Potpourri, although an air enhancing material 34 may comprise or include any material which may be imparted or added to air contacting the air enhancing material 34.

As perhaps best shown by FIG. 9, in some embodiments, the filter medium 31 may be coupled to the air inlet 21 so that atmosphere 201 (FIG. 8) passing through the air inlet 21 must pass through the filter medium 31. In this manner, the filter medium 31 may govern the entrance of atmosphere 201 into the cavity 15. Preferably, the filter medium 31 may be removably coupled to housing 11 proximate to the air inlet 21 so that atmosphere 201 passing through the air inlet 21 must pass through the removably coupled filter medium 31. In some embodiments, a filter medium 31 may be removably coupled to housing 11 by being slidably coupled to the housing 11 proximate to the air inlet 21 so that the perimeter of the filter medium 31 extends over and covers the entirety of the filter medium 31. An optional door 35 may also be removably coupled to the body 11 and be configured to control access to the filter medium 31. The filter medium 31 may be removed from the housing 11 by opening or removing the optional door 35 and retracting the filter medium 31 from the cavity 15 and out of contact with the air inlet 21 with the installation of the filter medium 31 being the reverse of removal.

In some embodiments, the device 100 may comprise a screen 36 which may be coupled to the air inlet 21, such as by being coupled to portions of the housing 11 proximate to the air inlet 21. A screen 36 may function to protect the filter medium 31 while still allowing atmosphere 201 to pass through the air inlet 21 and into the filter medium 31 so that the screen 36 is in fluid communication with the filter medium 31. In preferred embodiments, the screen 36 may be integrally formed with the housing 11. In alternative embodiments, the screen 36 may be integrally formed with the housing 11 by being cut into the housing 11. In further alternative embodiments, the screen 36 may be coupled to the air inlet 21 with adhesive or other fasteners.

Figure 6:
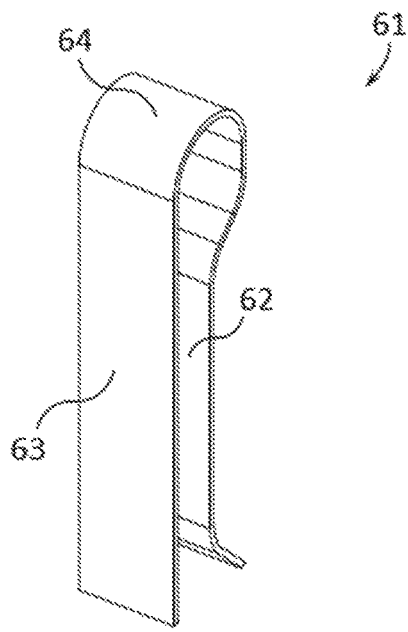
FIG. 6 shows a perspective view of an example of a structure anchor according to various embodiments described herein.
Figure 7:
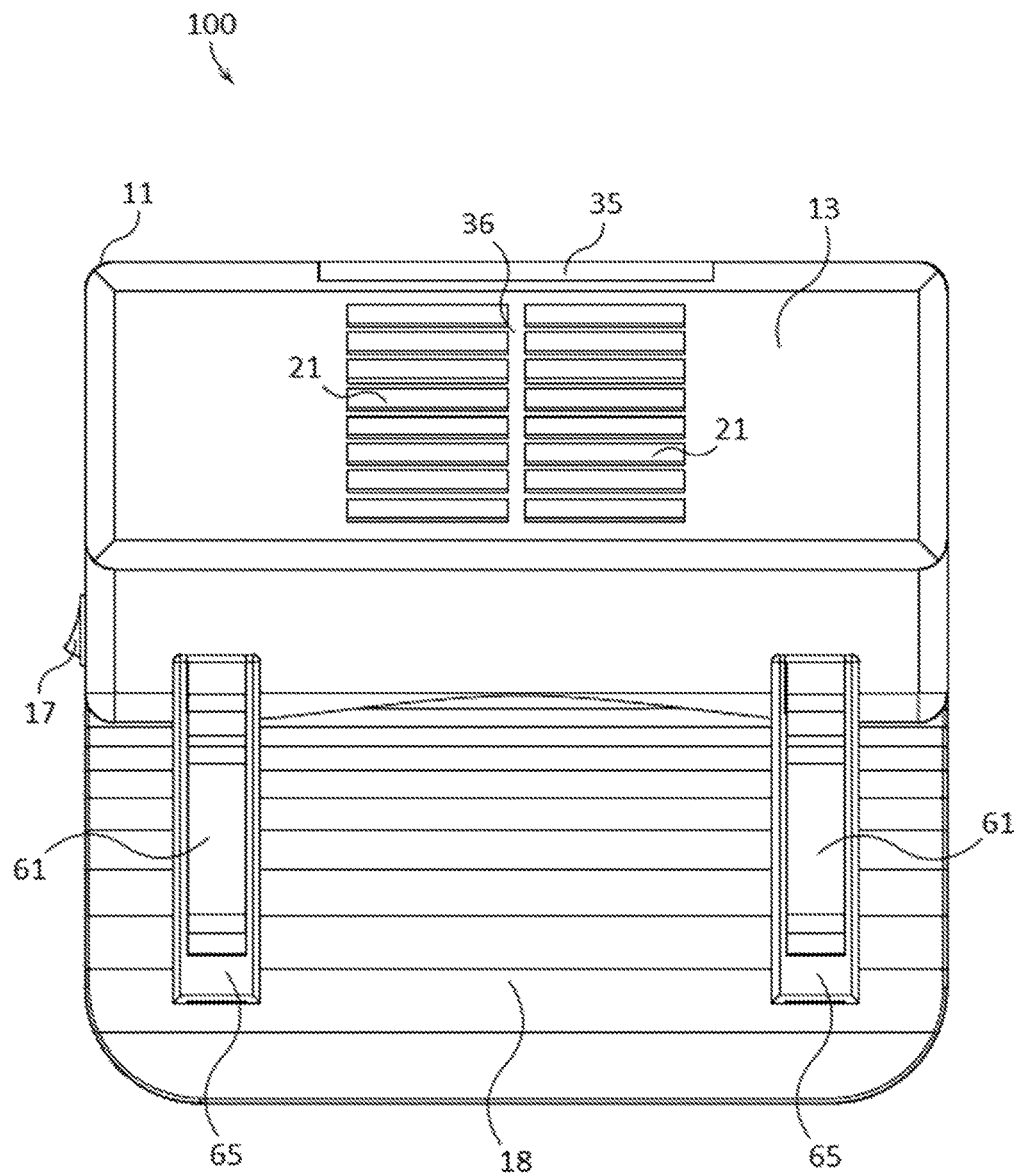
FIG. 7 depicts a rear elevation view of an example of an atmosphere conditioning device according to various embodiments described herein.

FIG. 6 shows a perspective view of an example of a structure anchor 61 according to various embodiments described herein. In some embodiments and as illustrated in FIGS. 2 and 7-9, the device 100 may comprise one or more structure anchors 61 which may be used to couple, optionally removably couple, the device 100 to a structure such as a chair, wall, and the like. In preferred embodiments, a structure anchor 61 may be configured as a clip-type fastener with a tensioning arm 62 and coupling arm 63 which may be tensioned together with a resilient hinge 64. The coupling arm 63 may be coupled to the housing 11 and/or an optional buttress 18 (FIGS. 1, 2, 7, 9, 10), while portions of the tensioning arm 62 may contact a structure such as a chair, wall, and the like, that the device 100 is to be coupled to. In this manner portions of the structure in contact with the tensioning arm 62 may be frictionally engaged or secured between the tensioning arm 62 and the housing 11 and/or an optional buttress 18. In alternative embodiments, a structure anchor 61 may comprise a strap or belt of flexible material which may be tied or otherwise coupled to a structure. In further alternative embodiments, a structure anchor 61 may comprise a fastener such as a clamp-type fastener, similar to a C-clamp or hose clamp for example, a screw type fastener, a hook and loop type fastener, or any other suitable type of fastener which may be configured to couple or removably couple the device 100 to a structure.

Referencing FIGS. 1, 2, 7, 9, 10 and in some embodiments, the device may comprise an optional buttress 18. A buttress 18 may be coupled to the housing 11 and may extend away from the housing 11. In some embodiments, a buttress 18 may be coupled to the perimeter 14, while in other embodiments, a buttress 18 may be coupled to the first side 12, second side 13, and/or perimeter 14. As perhaps best shown by FIGS. 1, 2, and 9, a buttress 18 may be generally planar in shape. In preferred embodiments, a buttress 18 may be generally curved planar in shape with a curve that is generally convex relative to the first side 12. The buttress 18 may comprise a generally planar shape which allows the buttress 18 to conform to portions of a user's upper back so that when the buttress 18 is contacting the back of the user, one or more air outlets 25, 26, are positioned proximate to the face, and preferably proximate to the nose and mouth, of the user. In further embodiments, a structure anchor 61 may be coupled to the housing 11 and/or an optional buttress 18 by way of an anchor receptacle 65 which may be a structure formed into or coupled to the portions of the housing 11 and/or an optional buttress 18 while also being coupled, preferably removably coupled, to the structure anchor 61, such as to a coupling arm 63.

Turning now to FIGS. 2 and 8, the device 100 may be configured to improve the air which may be breathed by a user. The device 100 may intake atmosphere 201, generally air which has not been processed by the device 100, and output conditioned air 202, generally air which has been processed by the device 100. In some embodiments, atmosphere 201 may enter an air inlet 21, optionally passing through a screen 36, and into a filter medium 31 in fluid communication with the air inlet 21, as the atmosphere 201 passes through the filter material 32 particulate matter is removed. Optionally, an air enhancing material 34 in or on the filter medium 31 may impart a fragrance, scent, or the like as the filter medium 31 processes the atmosphere 201 into conditioned air 202 which has been processed to remove particulate matter while optionally having acquired an air enhancing material 34. The conditioned air 202 may next pass through or be motivated by one or more air motivators such as a first air motivator 41 and a second air motivator 42. Conditioned air 202 from a first air motivator 41 may be communicated to an air outlet such as a first air outlet 25. In some embodiments, an optional first conduction conduit 27 may provide fluid communication between the first air motivator 41 and a first air outlet 25. Likewise, conditioned air 202 from a second air motivator 42 may be communicated to an optional second air outlet 26. In some embodiments, an optional second conduction conduit 28 may provide fluid communication between the first air motivator 41 and/or second air motivator 42 and a second air outlet 26. In further embodiments, the direction and/or amount of conditioned air 202 exiting an air outlet 25, 26, may be governed or controlled by one or more outlet governors such as a first outlet governor 51 and/or second outlet governor 52. In some embodiments, an optional first outlet governor 51 may be in fluid communication with a first air outlet 25 thereby allowing the first outlet governor 51 to control the direction and/or amount of conditioned air 202 exiting the first air outlet 25. In further embodiments, an optional second outlet governor 52 may be in fluid communication with a second air outlet 26 thereby allowing the second outlet governor 52 to control the direction and/or amount of conditioned air 202 exiting the second air outlet 26. Conditioned air 202 exiting the device 100 through one or more air outlets 25, 26, and optional outlet governors 51, 52, may decrease the air pressure within the cavity 15 thereby drawing atmosphere 201 into the device 100 according to the physics of fluid dynamic.

While some materials have been provided, in other embodiments, the elements that comprise the device 100 such as the housing 11, filter medium 31, first air motivator 41, optional second air motivator 42, optional conduction conduits 27, 28, optional frame 33, optional door 35, optional screen 36, optional outlet governors 51, optional structure anchor 61, optional buttress 18 and/or any other element discussed herein may be made from or comprise durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An atmosphere conditioning device, the device comprising:
   a housing having a cavity, a first side, a second side opposite to the first side, and a perimeter;
   an air inlet formed into the first side of the housing, wherein the air inlet is in fluid communication with the cavity;
   a filter medium coupled with the housing and in fluid communication with the cavity and the air inlet, wherein the filter medium governs the entrance of atmosphere into the cavity;
   a first air motivator in fluid communication with the cavity;
   a first air outlet disposed on the second side of the housing, wherein the first air outlet is in fluid communication with the first motivator;
   a second air motivator in fluid communication with the cavity;
   a second air outlet disposed on the second side of the housing, wherein the second air outlet is in fluid communication with the second air motivator; and
   wherein the first air outlet is disposed within a first protrusion and the second air outlet is disposed within a second protrusion, the first and second protrusion protruding outwardly away from the second side of the housing.

2. The device of claim 1, further comprising a clip-type fastener with a tensioning arm, wherein the clip-type fastener with a tensioning arm is coupled to the housing.

3. The device of claim 1, wherein the filter medium comprises an air enhancing material.

4. The device of claim 1, wherein the first protrusion is angled outwardly relative to the housing.

5. The device of claim 1 wherein the second protrusion is angled outwardly relative to the housing.

6. The device of claim 1, further comprising a curved buttress coupled to the perimeter of the housing, wherein the curved buttress extends away from and below the housing.

7. The device of claim 6, further comprising a structure anchor, wherein the structure anchor is coupled to the curved buttress.

8. The device of claim 1, further comprising a first conduction conduit, wherein the conduction conduit provides fluid communication between the first air motivator and the first air outlet, the first air motivator a bladeless fan.

9. The device of claim 1, wherein the filter medium is removably coupled to housing.

10. The device of claim 1, further comprising a screen coupled to the air inlet, wherein the screen is in fluid communication with the filter medium.

11. The device of claim 1, further comprising a first outlet governor rotationally coupled to the first air outlet, the first outlet governor comprising a directional aperture governed by a moveable flap.

12. An atmosphere conditioning device, the device comprising:
   a housing having a cavity, a first side, a second side, and a perimeter;
   an air inlet formed into the housing, wherein the air inlet is in fluid communication with the cavity;
   a filter medium coupled with the housing and in fluid communication with the cavity and the air inlet, wherein the filter medium governs the entrance of atmosphere into the cavity;
   a first air motivator in fluid communication with the cavity;
   a first air outlet and a second air outlet disposed on the first side of the housing, wherein the first air outlet and the second air outlet are in fluid communication with the first air motivator;
   a first outlet governor and a second outlet governor rotationally coupled to the housing so that by rotating the first and second outlet governors, a direction of conditioned air exiting the device may be changed along a first direction; and
   the first outlet governor comprising a first directional aperture governed by a first moveable flap and the second outlet governor comprising a second directional aperture governed by a second moveable flap, the first and the second movable flaps configured to change the direction of conditioned air exiting the device along a second direction, the second direction different from the first direction.

13. The device of claim 12, wherein the filter medium comprises an air enhancing material.

14. The device of claim 12, further comprising a clip-type fastener.

15. The device of claim 14, wherein the clip-type fastener comprises a tensioning arm and coupling arm.

16. The device of claim 12, further comprising a buttress coupled to the perimeter of the housing, wherein the buttress extends away from the housing.

17. The device of claim 16, further comprising a structure anchor, wherein the structure anchor is coupled to the buttress.

18. The device of claim 12, further comprising a first conduction conduit, wherein the first conduction conduit provides fluid communication between the first air motivator and the first air outlet.

19. The device of claim 12, wherein the filter medium is removably coupled to housing.

20. The device of claim 12, further comprising a screen coupled to the air inlet, wherein the screen is in fluid communication with the filter medium.

* * * * *